US008948783B2

(12) United States Patent
Pennanen et al.

(10) Patent No.: US 8,948,783 B2
(45) Date of Patent: Feb. 3, 2015

(54) USER ACTIVITY TRACKING SYSTEM

(71) Applicant: Facebook, Inc., Menlo Park, CA (US)

(72) Inventors: Juho Pennanen, Helsinki (FI); Aapo Kyrölä, Pittsburgh, PA (US); Juka Partanen, Helsinki (FI)

(73) Assignee: Facebook, Inc., Menlo Park, CA (US)

( * ) Notice: Subject to any disclaimer, the term of this patent is extended or adjusted under 35 U.S.C. 154(b) by 0 days.

(21) Appl. No.: 13/930,321

(22) Filed: Jun. 28, 2013

(65) Prior Publication Data

US 2015/0005030 A1    Jan. 1, 2015

(51) Int. Cl.
*H04W 24/00* (2009.01)
*H04W 4/00* (2009.01)

(52) U.S. Cl.
CPC .................................. *H04W 4/005* (2013.01)
USPC .................................. 455/456.1; 455/456.6

(58) Field of Classification Search
CPC .................................................. H04W 4/005
USPC ................ 455/414.1–414.3, 418–420, 404.1, 455/404.2, 456.1–457; 340/539.13, 340/988–996
See application file for complete search history.

(56) References Cited

U.S. PATENT DOCUMENTS

| | | |
|---|---|---|
| 7,171,268 B1 | 1/2007 | Kroll |
| 8,306,514 B1 | 11/2012 | Nunally |
| 2003/0065257 A1 | 4/2003 | Mault |
| 2010/0070456 A1 | 3/2010 | Sugihara |
| 2011/0161085 A1 | 6/2011 | Boda |
| 2012/0083714 A1 | 4/2012 | Yuen |
| 2012/0326873 A1 | 12/2012 | Utter |
| 2013/0123667 A1 | 5/2013 | Komatireddy |
| 2013/0190903 A1* | 7/2013 | Balakrishnan et al. ......... 700/91 |

FOREIGN PATENT DOCUMENTS

| | | |
|---|---|---|
| EP | 2 457 505 A1 | 5/2012 |
| JP | 2009-0217378 A | 9/2009 |
| KR | 10-2006-0037640 A | 5/2006 |

(Continued)

OTHER PUBLICATIONS

European Patent Office Search Report for Application 14174168.6-1870.

(Continued)

*Primary Examiner* — Ronald Eisner
(74) *Attorney, Agent, or Firm* — Baker Botts L.L.P.

(57) ABSTRACT

The present disclosure provides a system for tracking and recording movements of a communication device. The mobile communication device is operable to communicate one or more sensor signals to the system, wherein the sensor signals are indicative of motion associated with activities to which the user exposes the mobile communication device. The system includes a computing hardware that analysis sensor signals to classify them into one or more temporal zones, determines a most likely activity type associated with a given temporal zone, and sends the information regarding most likely activity to the mobile communication device. The user of the mobile communication device provides their confirmation whether the most likely activity type represents a correct analysis, and communicate the confirmation back to the computing hardware for amending parameters and/or algorithms which execute analysis of the sensor signals to improve their accuracy.

17 Claims, 6 Drawing Sheets

(56) References Cited

FOREIGN PATENT DOCUMENTS

| | | |
|---|---|---|
| KR | 10-2008-013602 A | 2/2008 |
| KR | 10-2009-0107161 A | 10/2009 |
| WO | 2010/096691 A2 | 8/2010 |
| WO | 2012/134797 A1 | 10/2012 |
| WO | 2012/170449 A1 | 12/2012 |

OTHER PUBLICATIONS

International Search Report and Written Opinion for International Application PCT/US2014/042839.
Non-Final Office Action for U.S. Appl. No. 13/930,347.

* cited by examiner

USER ACTIVITY TRACKING SYSTEM

CROSS-REFERENCE TO RELATED APPLICATIONS

This application is related to U.S. patent application Ser. No. 13/930,347, filed on 28 Jun. 2013, entitled "USER ACTIVITY TRACKING SYSTEM AND DEVICE", the disclosure of which is incorporated herein by reference in its entirety.

FIELD

The present disclosure generally relates to tracking, recording and analyzing user activities, and more specifically to systems and methods for identifying user activities based on sensor data collected by a mobile communication device of the user. Moreover, aspects of the disclosure are also directed to software products recorded on non-transitory machine-readable data storage media, wherein such software products are executable upon computing hardware, to implement the methods of the disclosure.

BACKGROUND

Tracking devices are known that sense and track user activities, especially sports activities. An example of a known activity tracking device is a wearable wristwatch device with a GPS receiver for tracking and analyzing 'running' activity of an associated user. Another example is a mobile application that utilizes GPS system of a respective mobile phone for recording movement of users while they exercise. Another example is a step counter used in shoes or attached to the user's clothes to collect the number of steps taken by the user. However, none of the existing tracking devices automatically sense, record, analyze and identify all types of user activities such as walking, running, jogging, cycling, rowing, driving with car, moving with bus, moving with train, walking stairs, running stairs, jumping, swimming, playing football, and skiing.

Nowadays, smartphones are equipped with an increasing number of sensors such as Global Positioning System (GPS) receivers, accelerometers, and proximity sensors, and smartphone users may find it interesting to have mobile applications that can automatically record, sense, analyze, and identify their activities. However, one of the key challenges in the automatic tracking of users' movements for the purpose of analyzing the type of activity is the classification of activity types. For example walking vs running activity may have only small difference in respect to the collected sensor data. Moreover, for the same activity, the sensor data may vary depending on how the smart phone is carried by the user. For example, the smartphone may be carried by the user in his/her hand, or in a pocket or in a backpack.

Hence, there is a need for an activity tracking solution that accurately senses and analyzes all kinds of user activities and that addresses the limitations of existing activity tracking solutions.

SUMMARY

The present disclosure provides a system for tracking and recording movements of a mobile communication device and a method of the using the same.

In one aspect, embodiments of the present disclosure provide a system for tracking and recording movements of a mobile communication device that includes one or more movement sensors and a wireless interface. The system includes a communication network for communicating with the mobile communication device and computing hardware for processing data supplied in operation from the mobile communication device. The mobile communication device communicates sensor signals to the system, wherein the sensor signals are indicative of motion associated with activities to which the mobile communication device is exposed by its user.

The computing hardware executes software products for analyzing the sensor signals to classify them into one or more temporal zones, and for analyzing the signals within each given temporal zone to determine one or more most likely activity types associated with the given temporal zone. The computing hardware further sends information indicating the most likely activity types associated with the temporal zones to the mobile communication device. The mobile communication device then requests its user to provide a confirmation whether or not the information indicating the most likely activity types associated with a temporal zone represents a correct analysis, and then communicates the confirmation back to the computing hardware for amending parameters and/or algorithms employed in the software products, which execute analysis of the sensor signals to improve their accuracy.

The system generates a temporal log of activities experienced by the mobile communication device, and presents the activities on a graphical user interface of a user in a timeline format.

The mobile communication device is implemented by way of at least one of: a portable computer such as a laptop, a smartphone, a wrist-worn phone, a phablet, a mobile telephone, a tablet computer, a portable media device or any other computing device that can be worn by the user and is capable of processing and displaying data. Moreover, one or more sensors of the mobile communication device are implemented using at least one of: a gyroscopic angular sensor, an accelerometer, a GPS position sensor, a cellular position sensor (i.e. using position derived/calculated in relation to one or more radio basestations (cellular and local area), a magnetometer, a microphone, a camera, a temperature sensor.

When executed on the computing hardware, the software products are operable to implement supervised or semisupervised classification algorithms such as neural networks, decision forest, and support vector machines, for analysis of information included in the sensor signals. As input, the supervised or semisupervised classification algorithms can use, for instance, the amplitudes of the frequency components of the information included in the one or more sensor signals, and the output of the classification algorithms are estimated probabilities of different activities, conditional on the sensor signals.

In another aspect, the mobile communication device includes a data processor for executing a mobile software application thereat, wherein the mobile software application is operable to cause a graphical user interface of the mobile communication device to present analyzed activity results provided from the computing hardware in a form of a timeline, wherein different analyzed activities are represented by mutually different symbols in respect of the timeline.

In yet another aspect, embodiments of the present disclosure provide a method of using the system for tracking and recording the movements of the mobile communication device.

In yet another aspect, embodiments of the present disclosure provide a mobile communication device for implementing the system for tracking and recording movements of the user.

Embodiments of the present disclosure sense, analyze and identify all types of user activities by analyzing the data collected from one or more sensors of a mobile communication device of a user. The identified activities are displayed on a graphical user interface of the mobile communication device in a timeline format. If the user disagrees/agrees with an identified activity, then they may provide their feedback and the feedback may be used to improve the analysis and identification of the activities for the next time. Thus, the accuracy of the analysis and identification of the user activities is optimized over time.

Additional aspects, advantages, features and objects of the present disclosure would be made apparent from the drawings and the detailed description of the illustrative embodiments construed in conjunction with the appended claims that follow.

It will be appreciated that features of the invention are susceptible to being combined in various combinations without departing from the scope of the invention as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the invention is not limited to specific methods and instrumentalities disclosed herein. Moreover, those in the art will understand that the drawings are not to scale. Wherever possible, like elements have been indicated by identical numbers.

DETAILED DESCRIPTION OF ILLUSTRATIVE EMBODIMENTS

The following detailed description illustrates embodiments of the disclosure and ways in which it can be implemented. Although the best mode of carrying out the invention has been disclosed, those in the art would recognize that other embodiments for carrying out or practicing the invention are also possible.

The present disclosure provides a system for tracking and recording movements of a mobile communication device that includes one or more movement sensors and a wireless interface. The system includes a communication network for communicating with the mobile communication device and computing hardware for processing data supplied in operation from the mobile communication device. The mobile communication device communicates one or more sensor signals to the system, wherein the sensor signals are indicative of motion associated with activities to which the mobile communication device is exposed by its user.

The computing hardware executes one or more software products for analyzing the sensor signals to classify them into one or more temporal zones, and for analyzing the signals within each given temporal zone to determine the most likely activity type associated with the given temporal zone. The computing hardware further sends information indicating the most likely activity types associated with the temporal zones to the mobile communication device. The mobile communication device then requests its user to provide a confirmation whether or not the information indicating the most likely activity types associated with the temporal zones represent a correct analysis, and then communicates the confirmation back to the computing hardware for amending parameters and/or algorithms employed in the software products that execute analysis of the sensor signals to improve their accuracy.

Figure 1:
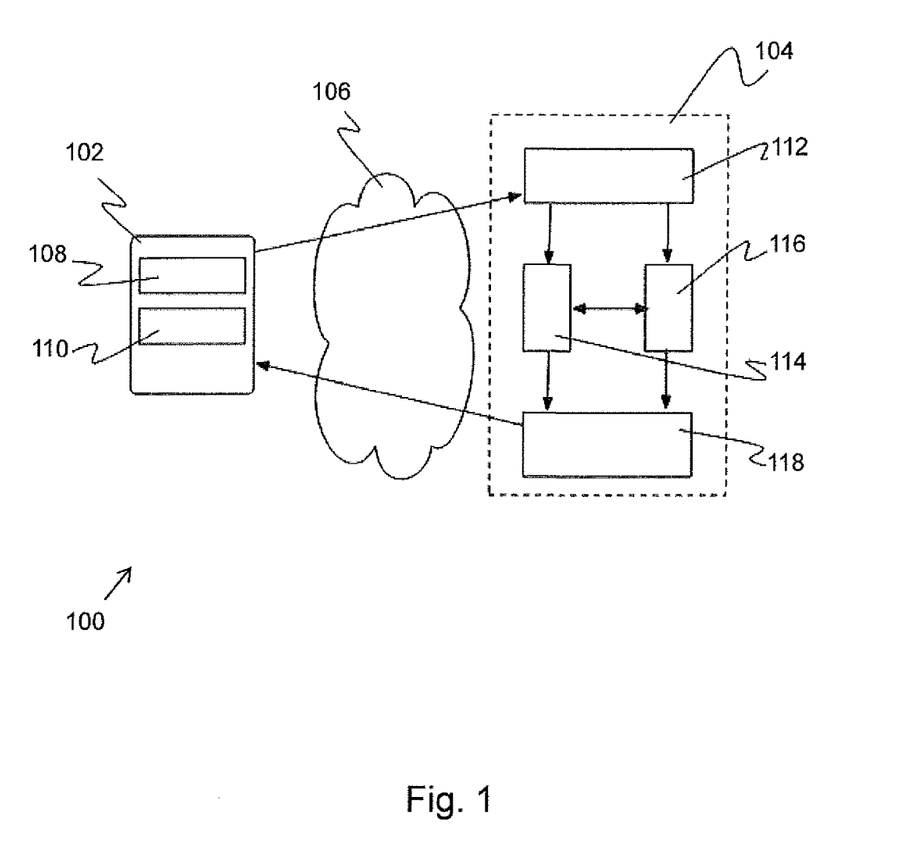
FIG. 1 is an illustration of a high-level architecture of a system that is suitable for practicing various implementations of the present disclosure.

Referring now to the drawings, particularly by their reference numbers, FIG. 1 is an illustration of a high-level architecture of a system 100 that is suitable for practicing various implementations of the present disclosure.

The system 100 includes a mobile communication device 102, and a server system 104 coupled in communication to the mobile communication device 102 by way of a communication network 106. The mobile communication device 102 is a handheld device of a user, and examples of the mobile communication device 102, include, but are not limited to, a smart phone, a wrist-worn phone, a phablet, a mobile telephone, a tablet computer executing operating systems such as Android, Windows, and iOS. The server system 104 includes a computing hardware that executes one or more software products for processing data supplied in operation from the mobile communication device 102. The server system 104 can be arranged as a cloud service or as dedicated servers located in a single site or at a plurality of mutually spatially distributed sites. Moreover, examples of the communication network 106 include, but are not limited to, a telecommunication network, and a WIFI network.

The mobile communication device 102 includes one or more sensors 108 and one or more positioning systems 110 to determine the position, movement, acceleration and/or environment of the mobile communication device 102, when a corresponding user performs one or more activities while carrying the device 102. Examples of such one or more activities, include, but are not limited to, walking, running, jogging, cycling, rowing, driving a car, moving with bus, moving with train, walking stairs, running stairs, jumping, swimming, playing football, and skiing. An example of the sensor 108 includes a motion sensor configured to measure the acceleration of the mobile communication device 102 in xyz-directions of a Cartesian co-ordinate system. Further examples of the sensor 108 include a gyroscopic angular sensor, a magnetometer, a microphone, a camera, and a temperature sensor. The positioning systems 110 are configured to determine the position of the mobile communication device 102 by implementing at least one of GPS positioning system, cell tower information for cellular networks, indoor positioning systems, WIFI fingerprinting and proximal WiFi networks. In an embodiment of the present invention, the mobile communication device 102 may periodically send the information collected by the sensors 108 and the positioning systems 110 to the server system 104 via the communication network 106.

The server system 104 includes a receiving module 112, a first processing module 114, a second processing module 116, and an output module 118. The receiving module 112 receives sensor and positioning data from the mobile communication device 102. The first processing module 114 executes a first process to analyze sensor data collected from the sensors 108, and the second processing module 116 executes a second process to analyze positioning data collected from the positioning systems 110. In an embodiment of the present disclosure, the first and second processes are parallel processes that might communicate with each other and also exchange data for analysis purposes. Based on the sensor data, the first processing module 114 generates an activity type of the user, and based on the positioning data, the second processing module 116 generates location and movement information pertaining to the activity. The output module 118 processes the activity type information and movement/location information of the activity to generate a summary/schedule of activities of the user. The output module 118 then sends the summary of activities to the mobile communication device 102 over the communication network 106.

The mobile communication device 102 includes a data processor (not shown) for executing a mobile software application thereat, wherein the mobile software application is operable when executed to cause a graphical user interface (GUI) of the mobile communication device to present summary of activities provided from the server system 104 in a timeline format. The user may send their positive/negative feedback on the summary of activities to the server system 104 and the server system 104 may receive, store and implement the feedback for improving their activity analysis.

In an embodiment of the present invention, some or all of the steps/analysis in the server system 104 may be implemented in the mobile communication device 102 based on the computing resources available in the mobile communication device 102.

FIG. 1 is merely an example, which should not unduly limit the scope of the claims herein. One of ordinary skill in the art would recognize many variations, alternatives, and modifications of embodiments herein.

Figure 2:
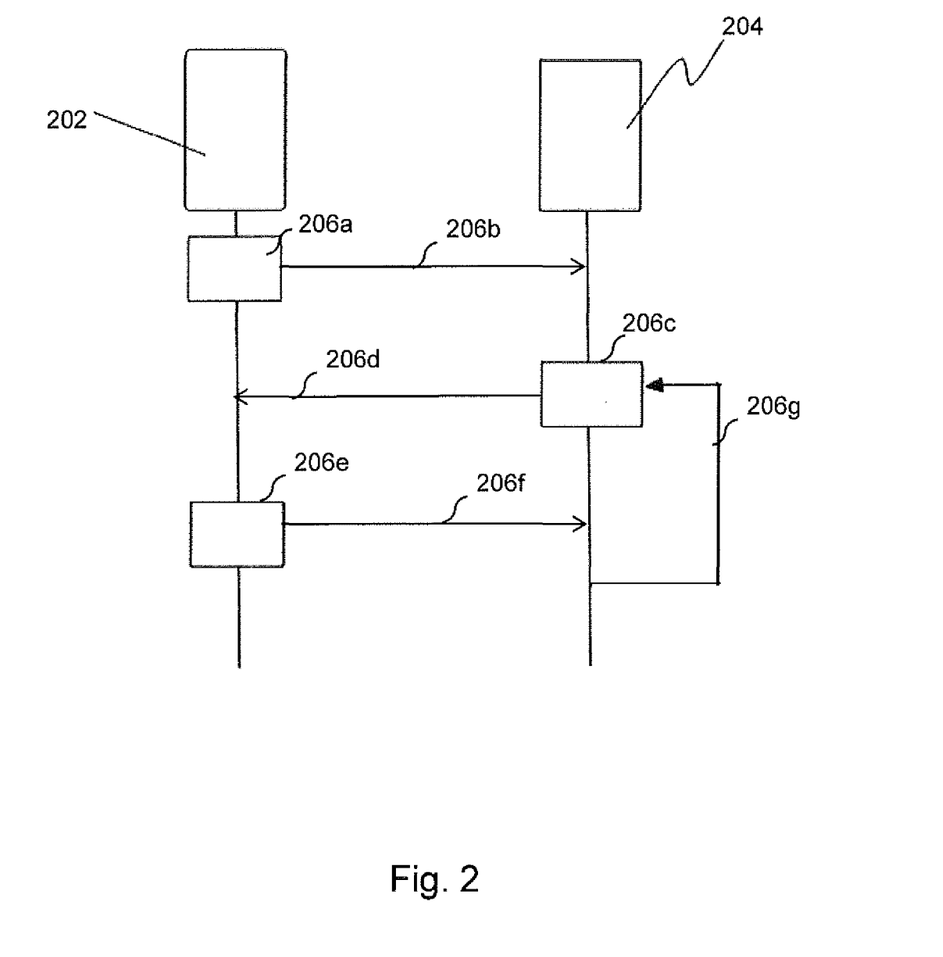
FIG. 2 is an illustration of an exchange of information between a mobile communication device and a computing hardware of FIG. 1, in accordance with the present disclosure.

FIG. 2 is an illustration of an exchange of information between a mobile communication device 202, and a server system 204 for tracking and analyzing activities of a user of the mobile communication device 202, in accordance with the present disclosure. The mobile communication device 202 and the server system 204 are examples of the mobile communication device 102 and the server system 104 respectively, and have been explained in conjunction with FIG. 1. A step 206a takes place at the mobile communication device 202, where the corresponding sensors and positioning systems measure sensor and positioning data when a corresponding user performs an activity. A step 206b represents transfer of sensor and positioning data from the mobile communication device 202 to the server system 204 for analysis of the user activity. In an embodiment, the mobile communication device 202 may send the sensor and positioning data continuously or in a buffered format. In another embodiment, the mobile communication device 202 may send the sensor and positioning data to the server system 204 in a raw format. In yet another embodiment, the mobile communication device 202 may process sensor and positioning data before sending to the server system 204. A step 206c takes place at the server system 204, where the server system 204 analyses the sensor and positioning data received from the device 202. In an embodiment of the present invention, the server system 204 may perform analysis based on a supervised classification and/or other machine learning algorithms and form a summary of activities of the user. A step 206d represents communication of summary of activities from the server system 204 to the mobile communication device 202. A step 206e takes place at the mobile communication device 202, where the summary of activities is displayed on a graphical user interface (GUI) of the mobile communication device 202. A step 206f represents a transfer of positive/negative feedback of the user on the summary of activities to the server system 204. Lastly, a step 206g represents implementation of the feedback by the server system 204 by modifying parameters and/or to selecting training data for the machine learning algorithms for providing a more accurate summary of activities in future. Examples of machine learning algorithms, for activity monitoring include, but are not limited to, supervised or semisupervised classification algorithms such as neural networks, decision forest, and support vector machines. The feedback is provided as an input to the machine learning algorithms and is used to modify parameters and select training data for the machine learning algorithms.

FIG. 2 is merely an example, which should not unduly limit the scope of the claims herein. One of ordinary skill in the art would recognize many variations, alternatives, and modifications of embodiments herein.

Figure 3:
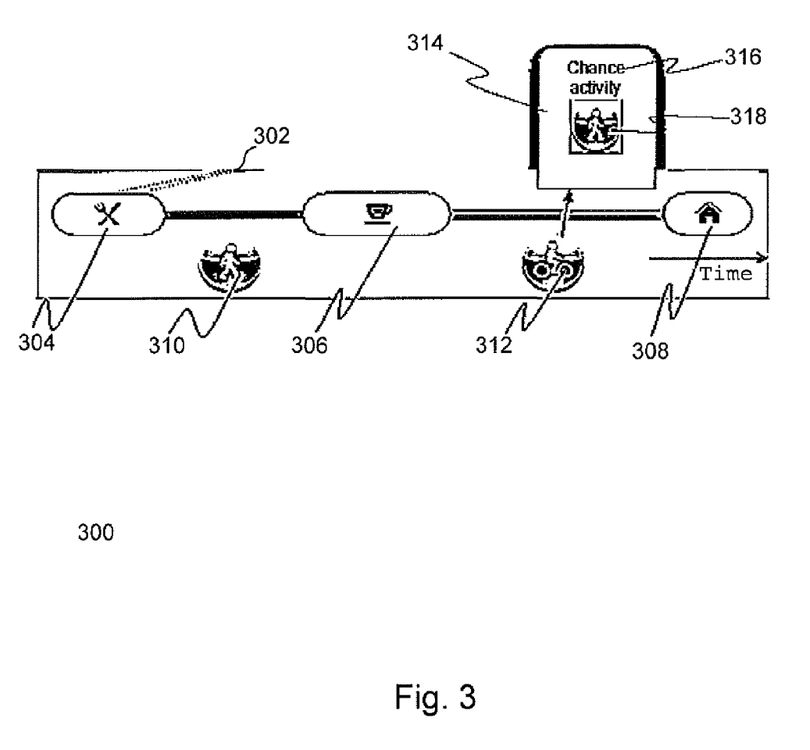
FIG. 3 is an illustration of a graphical user interface (GUI) of the mobile communication device, in accordance with the present disclosure.

FIG. 3 is an illustration of a graphical user interface (GUI) 302 of the mobile communication device 200, in accordance with the present disclosure, and has been explained in conjunction with FIG. 2.

The GUI 302 displays the summary of activities of a user (received from the server system 204 at the step 206d) in a time line format. In an exemplary embodiment, the GUI 302 displays location of the user by three location symbols, i.e. a restaurant symbol 304, a cafeteria symbol 306 and a home symbol 308, indicating that the user has visited the restaurant, cafeteria and home one after the other. The locations represented by the graphical symbols 304, 306 and 308 are identified based on the GPS system of the mobile communication device 202, cell tower information for cellular networks, indoor positioning systems, proximal WiFi, and/or WiFi fingerprinting. The GUI 302 further displays activities performed by the user by respective graphical symbols. In an example, a 'walking' activity symbol 310 is displayed between the restaurant 304 and cafeteria 306 to indicate that the user has walked from the restaurant to cafeteria. Further, a 'cycling' activity symbol 312 is displayed between the cafeteria 306 and the home 308 to indicate that the user has cycled from the cafeteria to home.

The story line display 302 may be a touch screen display and may be configured in a manner such that when a user touches or points an activity indication symbol such as the 'cycling' activity symbol 312, or a line above or an area close to the symbol 312, a pop-up menu 314 is presented. The pop-up menu 314 includes a text field 316 for enabling the user to modify the activity and a symbol field 318 for enabling the user to modify the graphical symbol pertaining to the activity. Similarly when a user touches or points a location symbol such as the 'restaurant' symbol 304, or a line above or an area close to the symbol 304, a pop-up menu (not shown) may be presented to modify the location. The modification of location/activity symbol by the user is communicated to the server system 204 as a feedback (step 206f).

FIG. 3 is merely an example, which should not unduly limit the scope of the claims herein. One of ordinary skill in the art would recognize many variations, alternatives, and modifications of embodiments herein.

Figure 4:
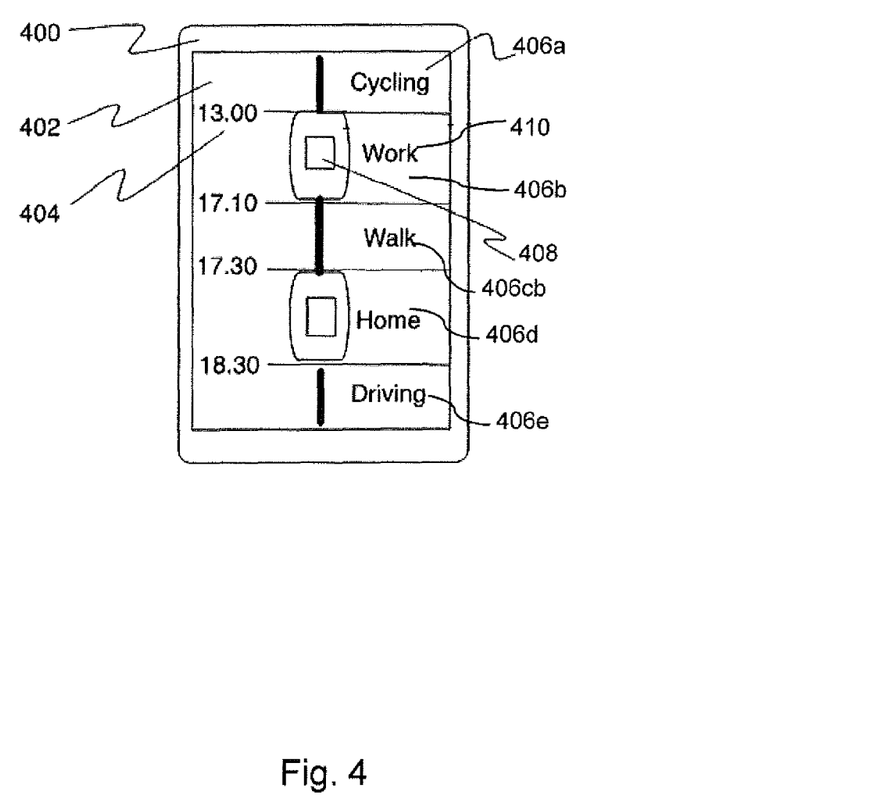
FIG. 4 is an illustration of an alternative layout of the GUI of the mobile communication device, in accordance with the present disclosure.

FIG. 4 is an illustration of a graphical user interface (GUI) 402 of a mobile communication device 400, which is an example of the mobile communication device 200, and has been explained in conjunction with FIGS. 2 and 3. The GUI 402 is an alternate layout of the GUI 302. The GUI 402 displays a time line 404 that is divided into 'activity' zones/periods 406a, 406b, 406c, 406d and 406e, hereinafter collectively referred to as activity zones 406, based on start and end time of one or more activities. Each activity zone 406 illustrates an activity and corresponding location of the activity. Further, each activity zone 406 may be illustrated by a graphical symbol 408 or a text description 410 of the corresponding activity.

In an exemplary embodiment, the timeline 404 indicates that at 13:00 pm, a 'cycling' activity of user ends and he/she is stationed at a 'workplace' until 17:10 pm; at 17:10 pm, the user starts a 'walking' activity towards home; at 17:30 pm, the user reaches home and is at home until 18:30 pm; at 18:30 pm, the user starts a 'driving' activity.

FIG. 4 is merely an example, which should not unduly limit the scope of the claims herein. One of ordinary skill in the art would recognize many variations, alternatives, and modifications of embodiments herein.

Figure 5:
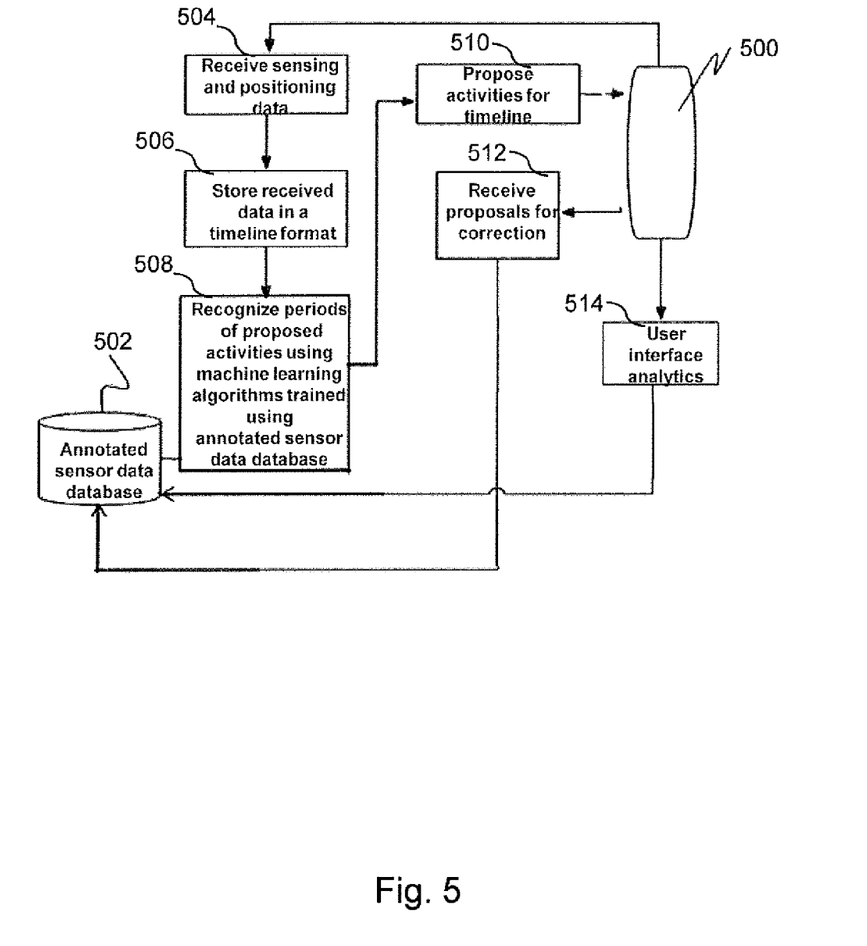
FIG. 5 is an illustration of steps of a method of determining activities of a user of a mobile communication device, in accordance with the present disclosure.

FIG. 5 is an illustration of steps of a method of determining activities of a user of a mobile communication device 500, in accordance with the present disclosure. The user activities are determined by an analysis logic module (not shown) which is supplied with the sensor and positioning data generated in operation by the mobile communication device 500, and an annotated sensor data database 502. The analysis logic module is communicatively coupled to the annotated sensor data database 502. In an embodiment of the present invention, the analysis logic module and the annotated sensor data database 502 may be present inside a remote server system. In another embodiment of the present invention, the analysis logic module and the annotated sensor data database 502 may be present inside the mobile communication device 500 itself.

At a step 504, the analysis logic module receives sensor and positioning data of the user from sensor and positioning systems of the mobile communication device 500. At a step 506, the analysis logic module stores the sensor and positioning data in a time line format in the annotated sensor data database 502, i.e. the sensor and positioning data is time stamped to record time and date of each or some of the collected data items. The annotated sensor data database 502 includes sensor and positioning data received from the mobile communication device 500, annotated with the information from user feedback on corresponding previously identified activities.

At a step 508, the analysis logic module analyzes the time line and delineates one or more activity periods and recognizes user activities in each activity period using different types of machine learning algorithms, which are trained using the data stored in the annotated sensor data database 502. For accurately identifying the activities, the analysis logic module may classify the annotated sensor and positioning data based on type of user, type of mobile device, type of user group, type of mobile device group, and demographic factors, etc. to take into account of environments and individual characteristics of the users. For example, acceleration data sensed by an accelerometer of the mobile communication device 500 for an active athletics specialized in long distance running may be different from the acceleration data sensed for a casual runner running very seldom. The active athletics may have longer steps with more predictable frequency between steps with lower variation of the frequency, than the casual runners. Therefore, for similar sensed data, the activity type may differ based on type of user group. Further, some mobile communication devices might have higher accuracy than others, therefore, for similar sensed data, the activity type may differ based on type of mobile communication device. The demographic classification may refer to segmenting users based on their gender, age, place of living etc, as the sensor data for a same activity might vary from person to person. The analysis logic module may further weigh the classified sensor data to take into consideration user specific features i.e. data could have weighted element consisting of average data from all users and user specific element from certain user based on the usage history.

At a step 510, the analysis logic module may use the classified sensor data to make a time line of the user activities, and communicate the time line to the mobile communication device 500. The mobile communication device 500 may display the time line on a user interface of the device 500. At a step 512, the analysis logic module may receive proposals for correcting one or more user activities in the timeline, from the mobile communication device 500. The proposals for correcting the user activities may be provided to the annotated sensor data database 502 for training of the machine learning algorithms.

At a step 514, the mobile communication device 500 may monitor whether or not the proposed time line has been viewed by the user using user interface analytics. If the user has viewed the proposed time line but not provided any correction in any activity of the timeline, then no feedback may be considered as positive feedback and is updated in the annotated sensor data database 502 that the analysis of one or more activities was correct and may be used as a training data for the algorithms. Further, if the user has viewed a storyline/timeline of a certain day and has been active in making corrections, one can conclude that that the recognized activities, which the user has not changed in the storyline, are probably considered to be correct and may be used as a training data for the algorithms. Further, it can be concluded that the recognized activities, which the user has changed in the storyline, are probably not correct. The amount of corrections made by users to certain activity can be used as a measure of recognition accuracy in regard to that activity. In the annotated sensor data database 502, the sensor data may be labeled, with a certain confidence of the labeling, based on the annotations containing information about user feedback on the corresponding proposed activities.

In an embodiment of the present invention, the analysis logic module may implement a first machine learning algorithm for determining user activities based on the sensor and positioning data, and newly introduce a second machine learning algorithm. However, if the data analyzed based on the second algorithm is more accurate than the data analyzed by the first algorithm, then the second algorithm may be determined to be priority algorithm over the first algorithm. This feature enables to test different setups and get "votes" on the capability of a machine learning algorithm.

It should be noted here that the steps 504 to 514 are only illustrative and other alternatives can also be provided where one or more steps are added, one or more steps are removed, or one or more steps are provided in a different sequence without departing from the scope of the claims herein.

Figure 6:
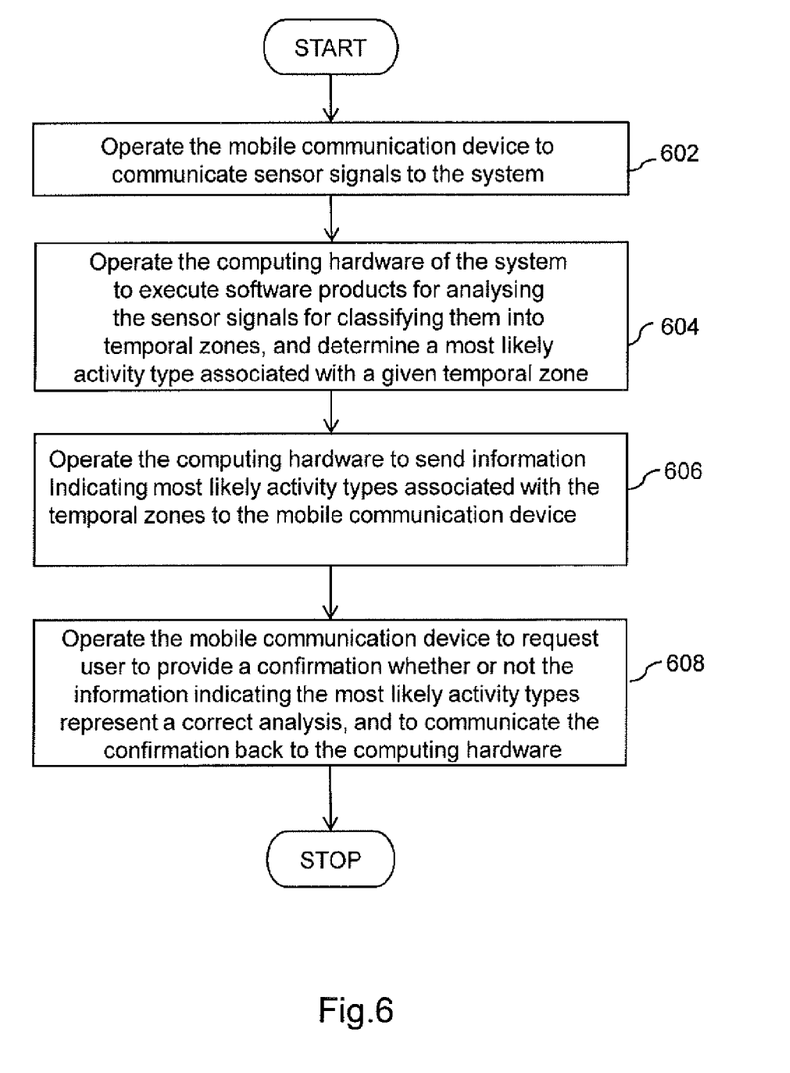
FIG. 6 is an illustration of steps of using a system for tracking and recording movements of the mobile communication device, in accordance with the present disclosure.

FIG. 6 is an illustration of steps of using the system 100 for tracking and recording movements of the mobile communication device 102, in accordance with the present disclosure, and has been explained in conjunction with FIGS. 1 and 2.

The method is depicted as a collection of steps in a logical flow diagram, which represents a sequence of steps that can be implemented in hardware, software, or a combination thereof.

At a step 602, the mobile communication device 102 is operable to communicate one or more sensor signals to the server system 104, wherein the sensor signals are indicative of motion associated with activities to which the mobile communication device 102 is exposed by its user. The sensor signals are output of one or more sensors of the mobile communication device 102.

At a step 604, the computing hardware of the server system 104 is operable to execute one or more software products for analyzing the sensor signals to classify them into one or more temporal zones, hereinafter referred to as activity zone, and for analyzing the sensor signals within each activity zone to determine a most likely activity type associated with the activity zone.

At a step 606, the computing hardware is operated to send information indicating one or more most likely activity types associated with the one or more activity zones to the mobile communication device 102.

At a step 608, the mobile communication device 102 is operable to request its user to provide a confirmation whether or not the information indicating the most likely activity types represent a correct analysis, and to communicate the confirmation back to the computing hardware for amending parameters and/or algorithms employed in the software products which execute analysis of the sensor signals to improve their accuracy.

It should be noted here that the steps 602 to 608 are only illustrative and other alternatives can also be provided where one or more steps are added, one or more steps are removed, or one or more steps are provided in a different sequence without departing from the scope of the claims herein.

Although embodiments of the current invention have been described comprehensively, in considerable detail to cover the possible aspects, those skilled in the art would recognize that other versions of the invention are also possible.

What is claimed is:

1. A system for tracking and recording movements of at least one mobile communication device, the mobile device including one or more movement sensors and a wireless interface, wherein the system includes a communication network for communicating with the at least one mobile communication device and computing hardware for processing data supplied in operation from the at least one mobile communication device, the system comprising:
    at least one mobile communication device operable to communicate one or more sensor signals to computing hardware of the system, wherein the one or more sensor signals are indicative of motion associated with activities to which the at least one mobile communication device is exposed by a user of the mobile communication device;
    computing hardware of the system operable to execute one or more software products for analyzing the one or more sensor signals to classify the one or more sensor signals into one or more temporal zones, and to analyze the one or more sensor signals within each given temporal zone to determine a most likely activity type associated with each given temporal zone,
    wherein the computing hardware is operable to send information indicating one or more most likely activity types associated with the one or more temporal zones to the at least one mobile communication device, and
    wherein the at least one mobile communication device is operable to request the user to provide a confirmation as to whether or not the information indicating the one or more most likely activity types associated with the one or more temporal zones represents a correct analysis, and to communicate the confirmation back to the computing hardware for amending parameters and algorithms employed in the one or more software products for analyzing the one or more sensor signals, in order to improve the accuracy of the software products.

2. The system as claimed in claim 1, characterized in that the system is operable to generate a temporal log of activities experienced by the at least one mobile communication device.

3. The system as claimed in claim 1, characterized in that the at least one mobile communication device is implemented by way of at least one of: a portable computer, a portable media device, a smart phone, a wrist-worn phone, a tablet, a mobile telephone, a tablet computer.

4. The system as claimed in claim 1, characterized in that one or more sensors of the at least mobile communication device are implemented using at least one of: a gyroscopic angular sensor, an accelerometer, a GPS position sensor, radio network based position sensor, a magnetometer, a microphone, a camera, a temperature sensor.

5. The system as claimed in claim 1, characterized in that the one or more software products are operable to implement when executed on the computing hardware at least one of:
    (a) a supervised or semisupervised classification analysis of information included in the one or sensor signals; and
    (b) a heuristic analysis of information included in the one or more sensor signals.

6. The system as claimed in claim 5, characterized in that the supervised or semisupervised classification analysis is operable to measure one or more frequency components of the information included in the one or more sensor signals for determining the amplitudes of the one or more frequency components at different points in time, wherein the amplitudes are used as input parameters to the supervised classification analysis and/or heuristic analysis.

7. The system as claimed in claim 1, characterized in that the at least one mobile communication device includes a data processor for executing at least one mobile software application thereat, wherein the at least one mobile software application is operable to cause a graphical user interface of the at least one mobile communication device to present analyzed activity results provided from the computing hardware in a form of at least one timeline, wherein different analyzed activities are represented by a plurality of mutually different symbols in respect of the at least one timeline.

8. A method of using a system for tracking and recording movements of at least one mobile communication device, the mobile device including one or more movement sensors and a wireless interface, wherein the system includes a communication network for communicating with the at least one mobile communication device, and the system includes computing hardware for processing data supplied in operation from the at least one mobile communication device, the method including:
    (a) operating the at least one mobile communication device to communicate one or more sensor signals to computing hardware of the system, wherein the one or more sensor signals are indicative of motion associated with activities to which the at least one mobile communication device is exposed by a user of the mobile communication device;

(b) operating the computing hardware of the system to execute one or more software products for analyzing the one or more sensor signals to classify the one or more sensor signals into one or more temporal zones, and to analyze the one or more sensor signals within each given temporal zone to determine a most likely activity type associated with each given temporal zone;

(c) operating the computing hardware to send information indicating one or more most likely activity types associated with the one or more temporal zones to the at least one mobile communication device; and (d) operating the at least one mobile communication device to request the user to provide a confirmation as to whether or not the information indicating the one or more most likely activity types associated with the one or more temporal zones represents a correct analysis, and to communicate the confirmation back to the computing hardware for amending parameters and algorithms employed in the one or more software products for analyzing the one or more sensor signals, in order to improve the accuracy of the software products.

9. The method as claimed in claimed in claim 8, characterized in that the method includes operating the system to generate a temporal log of activities experienced by the at least one mobile communication device.

10. The method as claimed in claim 8, characterized in that the method includes implementing at least one mobile communication device by way of at least one of: a portable computer, a portable media device, a smart phone, a wrist-worn phone, a tablet, a mobile telephone, a tablet computer.

11. The method as claimed in claim 8, characterized in that the method includes implementing the one or more sensors of the at least mobile communication device using at least one of: a gyroscopic angular sensor, an accelerometer, a GPS position sensor, a cellular position sensor, a magnetometer, a microphone, a camera, a temperature sensor.

12. The method as claimed in claim 8, characterized in that the one or more software products are operable to implement when executed on the computing hardware at least one of:
(a) a supervised or semisupervised classification analysis of information included in the one or sensor signals; and
(b) a heuristics analysis of information included in the one or more sensor signals.

13. The method as claimed in claim 12, characterized in that the method includes operating the supervised or semisupervised classification analysis to measure one or more frequency components of the information included in the one or more sensor signals for determining the amplitudes of the one or more frequency components at different points in time, wherein the amplitudes are used as input parameters to the supervised or semisupervised classification analysis.

14. The method as claimed in claim 8, characterized in that the method includes arranging for the at least one mobile communication device to include a data processor for executing at least one mobile software application thereat, wherein the at least one mobile software application is operable to cause a graphical user interface of the at least one mobile communication device to present analyzed activity results provided from the computing hardware in a form of at least one timeline, wherein different analyzed activities are represented by a plurality of mutually different symbols in respect of the at least one time line.

15. A non-transitory machine-readable data storage media storing a software product stored, wherein the software product is executable upon computing hardware of a mobile communication device for implementing a method as claimed in claim 8.

16. The non-transitory machine-readable data storage media as claimed in claim 15, characterized in that the software product is downloadable from a software application store to the portable device.

17. The mobile communication device for use when implementing the system as claimed in claim 1.

* * * * *

UNITED STATES PATENT AND TRADEMARK OFFICE
CERTIFICATE OF CORRECTION

| | | |
|---|---|---|
| PATENT NO. | : 8,948,783 B2 | Page 1 of 1 |
| APPLICATION NO. | : 13/930321 | |
| DATED | : February 3, 2015 | |
| INVENTOR(S) | : Juho Pennanen et al. | |

It is certified that error appears in the above-identified patent and that said Letters Patent is hereby corrected as shown below:

On the Title Page, at (72) Inventors: Before "Partanen" delete "Juka" and insert -- Jukka --.

Signed and Sealed this
Sixteenth Day of June, 2015

Michelle K. Lee
*Director of the United States Patent and Trademark Office*